United States Patent [19]

Cassell

[11] Patent Number: 5,461,824
[45] Date of Patent: Oct. 31, 1995

[54] METHOD FOR CONTROLLING TREE GROWTH

[75] Inventor: Ronald L. Cassell, New Palestine, Ind.

[73] Assignee: DowElanco, Indianapolis, Ind.

[21] Appl. No.: 284,703

[22] Filed: Aug. 2, 1994

Related U.S. Application Data

[63] Continuation of Ser. No. 927,081, Aug. 7, 1992, abandoned.

[51] Int. Cl.⁶ .......................... A01G 29/00; A01B 79/00
[52] U.S. Cl. ................... 47/57.5; 47/58; 504/239; 71/DIG. 1
[58] Field of Search ................... 47/57.5, 58; 504/239

[56] References Cited

U.S. PATENT DOCUMENTS

| | | | |
|---|---|---|---|
| 4,554,007 | 11/1985 | Funaki et al. | 504/274 |
| 4,655,001 | 4/1987 | Lepp et al. | 47/57.5 |
| 4,824,473 | 4/1989 | McVey et al. | 504/272 |
| 4,952,232 | 8/1990 | Cuomo et al. | 504/274 |

OTHER PUBLICATIONS

Shigo A. L., "Compartmentalization: A conceptual framework for Understanding how trees grow and defend therbis", Ann. Rev. Phytopathol. 1984, 22: 189–214.

Duncan et al., "Prolonged Infusion of Fluids into Tree Seedlings Using Ascorbic Acid", J. of Experimental Botany, vol. 41, 1379–83, (1990).

*Primary Examiner*—Peter O'Sullivan
*Assistant Examiner*—Deborah Lambkin
*Attorney, Agent, or Firm*—Donald R. Stuart

[57] ABSTRACT

Tree growth is suppressed by placing an implant below the bark layer of the tree at each of a plurality of sites spaced around the circumference of the trunk of the tree, each implant containing a unit dose of active ingredient selected from flurprimidol, paclobutrazol, and uniconazole.

9 Claims, No Drawings

METHOD FOR CONTROLLING TREE GROWTH

This is a continuation of application Ser. No. 07/927,081 filed Aug. 7, 1992 now abandoned.

This invention provides a new method for controlling the growth of trees.

In some areas, for example in areas beneath power lines, it is very desirable to suppress the growth of trees so that the required cutting cycle is lengthened and the biomass that must be removed is decreased. One chemical that has been used for this purpose is flurprimidol. Flurprimidol is the generic name for α-(1-methylethyl))-α-[4-(trifluoromethoxy)-phenyl]-5-pyrimidinemethanol:

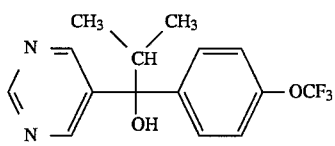

A second compound useful for this purpose is paclobutrazol. Paclobutrazol is the generic name for (2RS,3RS)-1-(4-chlorophenyl)-4,4-dimethyl-2-(1H-1,2,4-triazol-1-yl)pentan-3-ol:

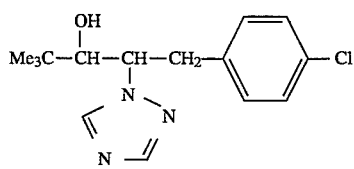

A third compound with similar utility is uniconazole. Uniconazole is the generic name for (E)-(RS)-1-(4-chlorophenyl)-4,4-dimethyl-2-(1H-1,2,4-triazol-1-yl)pent-1-en-3-ol:

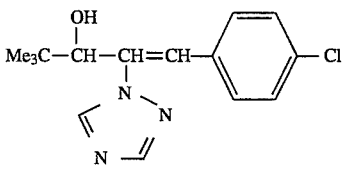

These compounds achieve growth suppression by inhibiting gibberellin biosynthesis and thereby reducing internodal elongation of terminal shoots.

As currently used, flurprimidol is injected into the trunks of trees under pressure in the form of a 7% alcohol solution. This method of application requires use of specialized equipment, is time consuming, and presents risks to both the tree and the applicator. The alcohol solution frequently causes the bark to split above the injection site. The splitting results in wounds that may not heal and in discoloration of bark, which is considered unsightly and is not desirable for trees along sidewalks. Further, preparation of solutions and handling of solutions under pressure exposes the applicator to contact with both the solvent and the active material.

This invention provides a new method for applying flurprimidol, paclobutrazol, or uniconazole that avoids the foregoing problems. More specifically, this invention provides a method for controlling the growth of a tree which comprises placing implants below the bark layer of the tree at each of a plurality of sites spaced around the circumference of the tree, each implant containing a unit dose of flurprimidol, paclobutrazol, or uniconazole.

The unit dose implants used in practicing this invention can be, for example, tablets, gelatin capsules, suppositories, or grease plugs. The implants can be formulated with other materials, provided the other materials do not unduly interfere with availability of the active ingredient for transport in the tree. In general, the implant will contain the active ingredient in a relatively concentrated form, i.e. in the range from 25–100% by weight. The preferred unit dose form is tablets.

Tablets used in practicing this invention preferably include a material that will promote disintegration of the tablet after it is placed in the tree, thereby increasing availability of the active material. Useful disintegrants include, for example, malodextrin, starch, pre-gelatinized starch, lactose, sorbitol, microcrystalline cellulose, and hydroxypropyl methylcellulose. A preferred disintegrant is pre-gelatinized starch.

The tablets used in practicing the present invention can be made using conventional tablet making technology. For example, a mixture of flurprimidol and a disintegrant can be compressed in a tablet press. In this case, it is advantageous to include stearic acid in the tablets to lubricate the tablet press and aid in release of the tablet from the die after it is formed.

Instead of using a tablet press, any other conventional tablet making technique, such as roll compacting, molding, or extruding, can be used.

It is desirable to keep the physical size of the tablet relatively small, so that only a small hole in the tree trunk is required to insert it. The required hole is desirably ⅜ inch or less. The size of the unit dose is not narrowly critical. As a practical matter, it will generally fall in the range of 0.1 to 2.0 g. Tablets containing 1 g of active ingredient are convenient.

| | |
|---|---|
| flurprimidol | 94.05% |
| pre-gelatinized starch | 4.50% |
| stearic acid | 1.0% |
| water | 0.45% |

The following detailed example illustrates preparation of tablets useful in practicing the invention.

EXAMPLE 1

A mixture of 2280 g of flurprimidol and 102 g of pre-gelatinized starch was sprayed with 75 g of water and mixed. The resulting tacky mixture was dried and 120° F. with mixing until a moisture content of about 0.5% was achieved. A second batch was made in the same way and combined with the first, producing 4696 g of flurprimidol/starch mixture. This mixture was dry blended with 17.61 g of stearic acid. This material was compressed into tablets using a Stokes tablet press to provide tablets containing 1.0 g. of flurprimidol.

EXAMPLE 2

A mixture of 15,000 g of flurprimidol and 397 g of pre-gelatinized starch was sprayed with 254 g of water and mixed. An additional 317.5 g of pre-gelatinized starch was then added to the mixture and blended. This mixture was combined with 158.7 g of stearic acid and mixed. The resulting mixture was compressed into tablets on a Stokes tablet press, with tablet weight adjusted to provide tablets containing 1.0 g of flurprimidol. The tablets were allowed to dry at room temperature to a final moisture content of approximately 0.50% by weight.

In accordance with the invention, the flurprimidol, paclobutrazol, or uniconazole is applied to a tree by placing unit dose implants containing the active ingredient in the trunk of the tree below the bark level. This is preferably accomplished by drilling holes at spaced intervals around the circumference of the tree. The holes are of such a size as to allow the implant to be inserted without force to a depth just below the bark layer. One inch below the bark level is suitable. Preferably the holes are drilled at a slight downward angle into the tree to reduce sap flow out of the hole. It is desirable to keep the hole diameter as small as possible to reduce damage to the tree. A ⅜" self-centering (brad point) spiral bit is suitable. Each hole should preferably be filled or flushed with water prior to implant insertion. After the tablet is inserted, the hole can be sealed with a plug of, for example, hardwood or latex calking material to prevent insect or other pathogen entry. Sealing the hole is not required in all cases, because the tree will seal the wound within the first year. If caulking is used, pressure should not be applied to enclose the implant, as this would prevent the active ingredient from being available for transport in the tree.

To assure uniform control, it is desirable for holes to spaced evenly around the complete circumference of the tunk near the ground line. Areas to avoid are regions directly over girdling roots or adjacent to trunk damage abrasions. Whenever possible, implants should be placed directly above a butress root in the crown of the flare. If a large flare exists, two implants may be placed in the same flare. While the ideal implant spacing is about six to eight inches, the spacing can be altered to avoid centering in the sinus between butresses.

The number of holes drilled around the circumference of the tree depends on the desired application rate and the amount of active ingredient in each tablet. Preferred application rates depend on the tree and on crown size relative to trunk size. Trunk size is conveniently measured in terms of the diameter of the trunk 4 feet above the ground (dbh).

The application rate will generally be in the range between 0.01 and 4.0 g of the active ingredient per inch of tree diameter (dbh). The abbreviation dbh refers to diameter at breast height. The rates at the low end of this range are much lower than those required by the previous injection method.

If flurprimidol or paclobutrazol is used, an application rate of 0.5 to 0.75 g/in dbh is preferred for the trees identified in the following table as belonging to "Group 1". If uniconazole is employed, slightly higher rates are suitable.

| Group 1 Tree Species | |
| --- | --- |
| Alder, Red | Ash |
| Black Olive | Black Cherry |
| Black Locust | Black Walnut |
| Box Elder | Dogwood |
| Elm, American | Elm, Chinese |
| Elm, Siberian | Elm, Winged |
| Blue Gum Eucalyptus | Hackberry |
| Maple, Norway | Maple, Red |
| Maple, Silver | Maple, Sugar |
| Oak, Laurel | Oak, Live |
| Oak, Pin | Oak, Post |
| Oak, Red | Oak, Southern Red |
| Oak, Water | Oak, Willow |
| Sugarberry | Sweetgum |

If flurprimidol or paclobutrazol is used, an application rate of 1.0 to 1.50 g/in dbh is preferred for the trees identified in the following table as belonging to "Group 2". Again, if uniconazole is employed, slightly higher rates may be used.

| Group 2 Tree Species | |
| --- | --- |
| Aspen | Sycamore |
| Cottonwood | Willow, Black |
| Melaleuca | |

Trees which have been heavily pruned and have small crowns relative to trunk diameter should receive an amount of active material at the low end of the range applicable to the relevant tree species.

The method provided by this invention is particularly applicable to deciduous trees as opposed to conifers such as pine, spruce, fir, or juniper.

After they are placed beneath the bark layer in a tree, the tablets dissolve, releasing the flurprimidol into the tree. Surprisingly, an effective amount of the active material is translocated through the xylem to the terminal shoots, where it must be delivered to suppress growth.

The tree implants may be installed at any time of year; however, best results are achieved when the implants are placed in the tree during active growth or 2–3 months prior to active growth. The most rapid uptake and translocation occurs from treatments made from two months prior to spring budbreak until leaves are fully developed. During periods when trees are in full leaf, best results may be obtained if installation is made when moisture stress is low. This can be accomplished by installing implants after significant rainfall or irrigation, or in early morning to avoid moisture stress induced by transpiration moisture loss in mid-day. Where pruning is required, best results may be achieved when application is made prior to or in conjunction with pruning. Growth suppression may not be evident until the year following treatment. Repeat applications can be made once growth regulator effects start to decline. In follow-up treatments, reduced application rates may be required to avoid over-regulation of terminal growth.

The application method of this invention has numerous significant advantages. The biomass produced by the trees is reduced, the cutting cycle in lengthened, and the foliage of the trees is improved. Compared to the current application method, the amount of time required to treat a tree is reduced by perhaps 90%. Equipment requirements are minimized. There is no lasting damage to the tree, as occasionally occurred with the injection of alcohol solutions. Exposure of the applicator is greatly reduced, and handling of flammable liquids is eliminated.

Field Trial Results

Flurprimidol tablets were implanted in a variety of tree species, using the application rates recommended above. The following data parameters were subsequently measured:

1) green weight/volume of trimmed biomass for treated versus untreated trees.

2) growth reduction of treated versus untreated trees.

In general, no significant effects were noted in the first year following treatment; but as measured in the third growing season, greenweight/volume of biomass was 68% lower on average for treated trees (range of 51–98% across species and locations) and growth reduction of treated versus untreated trees averaged 62% (range of 40–80% across species and locations).

I claim:

1. A method for delivering to the terminal shoots of a tree a growth supressing amount of flurprimidol, which comprises placing an implant below the bark layer of the tree at each of a plurality of sites spaced around the circumference of the trunk of the tree, each implant containing a unit dose of flurprimidol.

2. The method of claim 1 wherein the implant is of suitable size and shape so that it can be inserted into a ⅜ inch diameter or smaller hole.

3. The method of claim 1 wherein the implant contains a 0.1 to 2.0 g dose of the active ingredient.

4. The method of claim 1 wherein the implant contains a 1.0 g dose of the active ingredient.

5. The method of claim 1 wherein the implant comprises 25 to 100% by weight of the active ingredient.

6. The method of claim 1 wherein the unit dose implants are tablets.

7. The method of claim 6 wherein the tablets include pre-gelatinized starch.

8. The method of claim 1 wherein the application rate is in the range from 0.01 to 4.0 g/in dbh.

9. The method of claim 1 wherein the application rate is in the range from 0.01 to 1.5 g/in dbh.

* * * * *